United States Patent [19]
Truax

[11] Patent Number: 5,683,244
[45] Date of Patent: Nov. 4, 1997

[54] DENTAL APPLIANCE TO CORRECT MALOCCLUSION

[76] Inventor: Lloyd H. Truax, 15 Seventh Ave. NW., Rochester, Minn. 55901

[21] Appl. No.: 500,811

[22] Filed: Jul. 10, 1995

[51] Int. Cl.⁶ ................................. A61C 7/00
[52] U.S. Cl. .............................. 433/6; 433/24
[58] Field of Search ................... 433/6, 19, 24, 433/5; 128/848, 859

[56] References Cited

U.S. PATENT DOCUMENTS

| | | |
|---|---|---|
| 4,396,373 | 8/1983 | Dellinger ............... 433/19 |
| 4,439,149 | 3/1984 | Devincenzo ............. 433/6 |
| 4,505,672 | 3/1985 | Kurz ................... 433/6 |
| 4,619,609 | 10/1986 | Clark ................. 433/6 |
| 4,671,767 | 6/1987 | Blechman et al ........ 433/19 |
| 4,810,192 | 3/1989 | Williams .............. 433/6 |
| 5,267,862 | 12/1993 | Parker ................ 433/215 |
| 5,499,633 | 3/1996 | Fenton ................ 433/6 |

*Primary Examiner*—Cary E. O'Connor
*Attorney, Agent, or Firm*—Malcolm D. Reid

[57] ABSTRACT

A dental appliance to correct a malocclusion of a dental patient, have upper and lower pieces that orthodontically fit in the mouth of the patient in engagement with selected upper and lower teeth of the patient. The dental pieces have interlock means that hold them together with the jaws in a position of correction. Occlusal surfaces can be provided to permit chewing of food while the appliance is worn.

16 Claims, 3 Drawing Sheets

DENTAL APPLIANCE TO CORRECT MALOCCLUSION

BACKGROUND OF THE INVENTION

A proper fit of the occlusal surfaces of the teeth is necessary for proper biting and chewing as well as desirable facial features. A proper fit is a function of the relative positions of the teeth and the mandible and maxilla, the lower and upper jaws, either of which maybe retruded or protrdded. Permanent teeth may be removed to mask this dental and skeletal discrepancy. Jaw surgery is another way of correcting this functional and facial esthetic problem. However, removable or fixed appliances may accomplish the dental and skeletal changes without removal of permanent teeth and without jaw surgery. These appliances are particularly effective during adolescent growth and development and to a lesser extent after full maturation. The maxilla is fixed to the skull. The mandible is attached to the skull by numerous muscles which power its movement. The mandible articulates at its posterior upward extremities with the temporal bone to form the jaw joint. This is necessarily a loosely connected joint in order to accommodate the substantial variety of movements of the mandible relative to the maxilla during biting and chewing procedures. The numerous muscles attaching the mandible to the skull control and power the complex movements involved in biting and chewing.

A so-called balanced occlusion is necessary for proper chewing and for desirable facial features. This involves balanced, simultaneous contacting of the upper and lower teeth on the right and left hand sides, and in the anterior and posterior occlusal areas. An unbalanced occlusion, a malocclusion, is disruptive of the proper biting and chewing functions. Correction of a malocclusion is of great benefit to the dental patient.

SUMMARY OF THE INVENTION

A new removable dental appliance and method to improve the relationship of the upper and lower teeth and their supporting bone to each other. This appliance consists of two parts, the lower fits over the mandibular teeth and the upper fits over the maxillary teeth, as well as the supporting alveolar bone and, in most cases, the palate. Expansion screws may be included to change the transverse and/or sagittal shape of one or both dental arches and the expansion screws may move teeth in the individual arch. To change a class II sagittal relationship, the mandible is brought forward the desired amount (a large discrepancy may require two or three steps) and a bite (usually wax) and a jaw relationship recording is taken. The appliances are constructed so the posterior occlusal surfaces of both appliances are flat and opposed to each other. The anterior teeth of one or both arches may also be covered. The mandible is brought forward and the jaws are closed. To maintain this forward position, a wedge is made on the cuspid or first premolar areas. The opposing appliance has a groove that fits the wedge. For the occlusal surfaces to fit together in this wedge and groove relationship, the mandible must be brought forward. Otherwise, there isn't a fitting together of the occlusal (biting and chewing) surfaces. At first, light force elastics are placed form the anterior labial position of the maxillary appliance to the buccal posterior portion of the mandibular appliance (class II elastics). These elastics aid in the forward positioning of the mandible. After a month or tow, the mandible will be positioned forward without the aid of elastics. The elastics are not necessary, but are helpful. Adjustments to position the mandible further forward (which will interchange the dental and skeletal relationship) are easily made. To position the mandible forward, the groove on the occlusal surface is positioned posteriorly. This is accomplished by removing material 2–3 mm distal to the original groove the same depth as the original groove. New soft material (acrylic or Triad, a trademark of Dentsply Inc.) is placed in the anterior part of this new expanded groove. A Vaseline coating is placed on the wedge of the upper appliance. The mandibular and maxillary appliances are placed in the mouth. The patient brings the mandible forward the desired amount and bites the occlusal surfaces together. The new groove is formed with the mandible advanced to a new position. The acrylic or Triad material is cured in a 20–30 minute office visit. A new appliance is not necessary. The mandible is positioned forward again if necessary in three to four months.

With the wedge and groove in the occlusal surface of the upper and lower appliance, there is a very definite and easy place to position the mandible forward to correct a class II malocclusion. The upper and lower occlusal surfaces are in total occlusion when biting together. This makes it easier to chew and to be left in during eating. Treatment time is reduced because the appliance is left in more (all the time) during function.

IN THE DRAWINGS

DESCRIPTION OF THE PREFERRED EMBODIMENT

Figure 1:
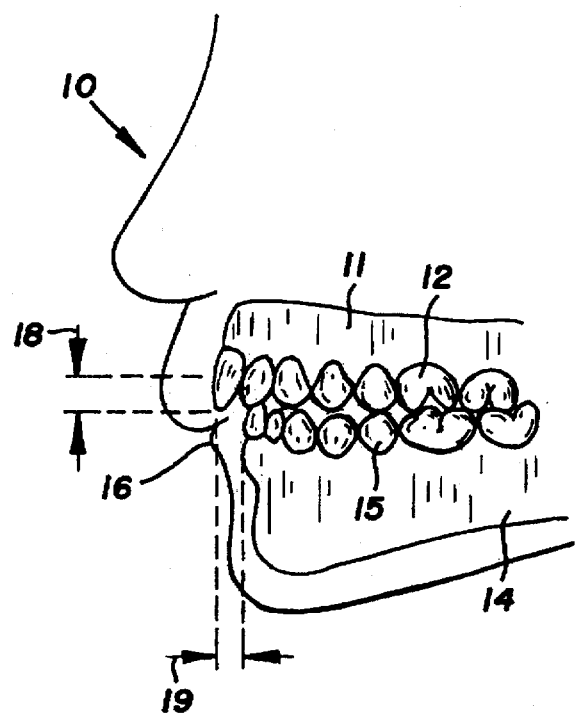
FIG. 1 is a side elevational view illustrating a patient with a closed mouth, having upper and lower teeth with a malocclusion, exhibiting both abnormal overjet and overbite and a retruded mandible and teeth.

Referring to the drawings, there is shown in FIG. 1, a dental patient with a class II malocclusion indicated with number 10 with drawing portions broken away for purposes of illustration. Patient 10 has a maxilla or upper jaw 11 with the usual array or set of upper or maxillary teeth 12, and a mandible or lower jaw 14 having lower or mandibular teeth 15. The teeth can also be classified as anterior and posterior. The anterior teeth, or anteriors, are those positioned frontally with respect to the lips 16, and include the central and lateral incisors and the canines of both the upper and lower arches. Remaining teeth, upper and lower, are the posterior teeth, or posteriors, including the bicuspids and molars.

Dental patient 10 exhibits an abnormal occlusion or malocclusion. This might be protrusive, retrusive, or lateral. In any case, correction of the abnormal occlusion will generally be beneficial to the patient in terms of improved chewing ability and improving facial aesthetics. Correction is accomplished with the dental appliance of the present invention by training the facial and masticatory muscles connecting the mandible to the skull, to differently position the mandible relative to the maxilla from the original, abnormal positional relationship to one that approaches and hopefully meets a normal position.

With respect to the particular patient 10, illustrated in FIG. 1 the patient has a retrusive occlusion characterized by excessive overbite and excessively overjet. Overbite is the vertical overlap of the upper and lower teeth, and overjet is the horizontal overlap of the upper teeth over the lower teeth. The over bite condition of patient 10 is indicated at 18 in FIG. 1, and overjet at 19. The condition persists by virtue of a rearward deviation of the lower jaw relative to the upper jaw, from the position of normal occlusion with normal overjet and overbite. The lower teeth are displaced from a position of normal occlusion with respect to the upper teeth by an amount referred to herein as an occlusal deviation. In order to correct for the condition without the continued use of a prosthetic device or jaw surgery, the lower jaw must preferably be moved a distance slightly over-correcting the occlusal deviation. The facial and masticatory muscles are trained to hold the lower jaw to the new position without conscious effort on the part of the patient. With this new position of the mandible, the teeth and the jaw relationship will change from abnormal to normal or nearly normal. The dental apparatus of the present invention accomplishes this.

Figure 3:
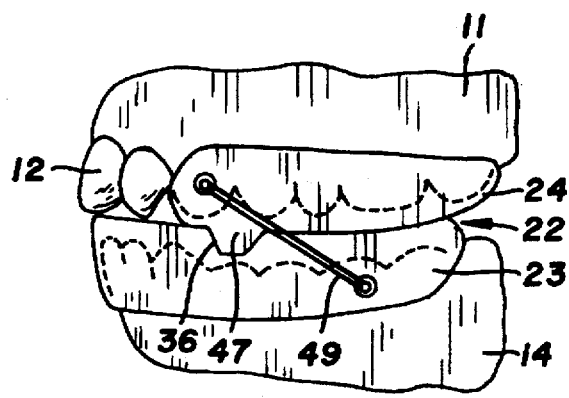
FIG. 3 is a side elevational view of the dental appliance of the invention worn by a patient requiring an intermediate correction due to a large discrepancy.
Figure 4:
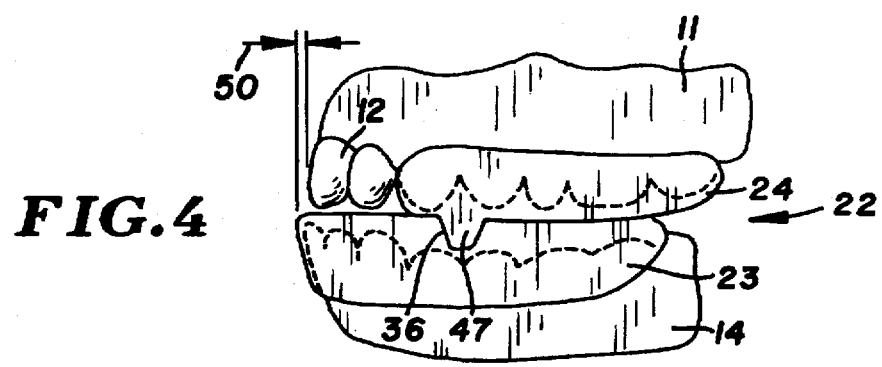
FIG. 4 illustrates a dental appliance according to the present invention installed in the mouth and upon the teeth of the patient, holding the mandible and maxilla in a final stage with a slight overcorrection to compensate for settling.

A dental appliance of the invention is shown in fitted and operative relationship to the teeth and jaws of a dental patient in FIG. 3 and 4, and is indicated generally at 22. Appliance 22 includes a lower piece 23 and an upper piece 24. The upper piece is shaped to fit in relatively secure relationship to the upper teeth and jaw. Correspondingly, the lower piece is shaped to fit in secure relationship to the lower teeth and jaw. Interlocking means on the upper and lower pieces are provided to restrain relative movement between them when they are brought together in a closed orientation. The interlocking means is provided in order to hold the upper and lower jaws in a predetermined relative relationship for an extended period of time for the purpose of correcting an abnormal occlusion.

Figure 5:
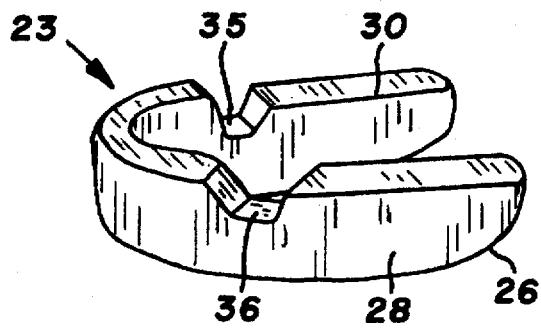
FIG. 5 is an upper perspective view of the lower piece of the dental appliance of the invention.
Figure 7:
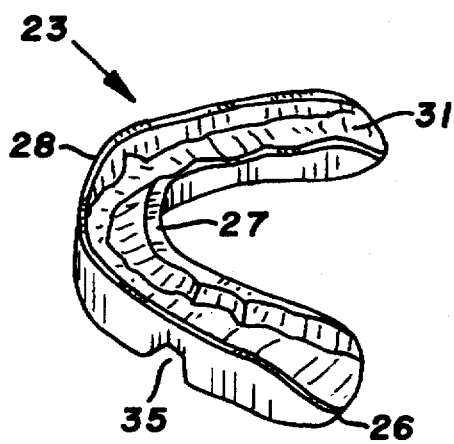
FIG. 7 is a perspective view showing the under portion of the lower piece of the dental appliance shown in FIG. 5.

Each appliance 22 is specifically fabricated to fit the unique jaw and mouth of the individual patient, and in accordance with the correction needed by that patient. FIGS. 5 and 7 illustrate a typical lower piece 23 of an appliance 22. An arch-shaped body portion 26 is constructed to closely conform to the lower dental arch of the patient. An interior side wall 27 and an outside wall 28 form a channel that accommodates the teeth and adjacent gum and jaw portions of the user. A top wall 30 connects the side walls 27, 28. The interior surface of top wall 30 has a plurality of pockets 31 which are shaped and positioned for receipt and accommodation of the ends of the lower teeth 15. The body 26 of lower piece 23 is constructed to cover most of the lower teeth including the molars. This retains lower piece 23 in place with respect to the lower jaw. This could be accomplished by engagement of less than the entire lower dental set, as might be indicated for a particular patient.

As shown in FIG. 5, the upper posterior expanses of the top wall 30 form occlusal surfaces to permit chewing food by the patient while wearing the appliance. The anterior portion is narrowed in accordance with the shape of the anterior teeth and also to facilitate the mechanics of biting and chewing. Intermediately or post-anteriorally positioned along the upper wall 30 of the lower section 23 are symmetrical indents or grooves 35, 36. These grooves, 35, 36 are part of the interlocking means provided in order to hold the first and second pieces of the dental appliance in relative position with respect to one another in order to hold the jaw in adjusted position.

Figure 6:
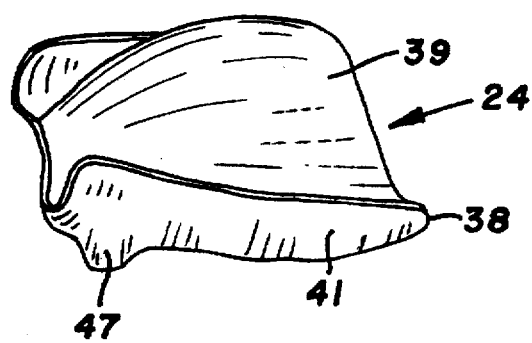
FIG. 6 is an upper perspective view of the upper piece of the dental appliance of the invention.
Figure 8:
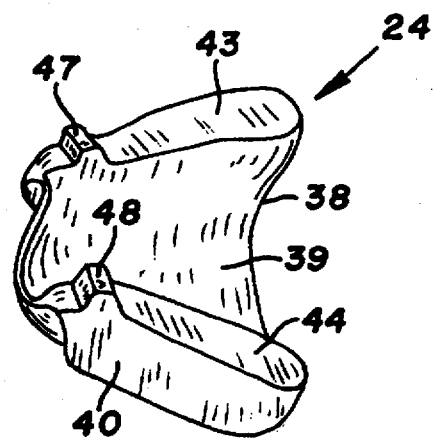
FIG. 8 is a perspective view showing the under portion of the upper piece of the dental appliance shown in FIG. 6.

As shown in FIGS. 6 and 8, the upper piece 24 has a body portion 38 characterized by a curved plate 39 contoured to fit in the roof of the mouth of the recipient. The upper piece 24 may also be fabricated to cover the upper teeth but not the roof of the mouth of the recipient. Bottom walls 43, 44 extend from the lower edges of the roof 39. Side walls 40, 41 extend upwardly from the bottom walls 43, 44 (FIG. 8). The channel between the side walls 40, 41 and the lower edge portions of the plate 39 accommodates posterior teeth of the recipient in relatively secure relationship. End walls 43, 44 present downwardly facing occlusal surfaces that are usable in the mechanics of chewing food.

Dentents or wedges 47, 48 are forwardly positioned on the end walls 43, 44 of the upper piece 24. Wedges 47, 48 are shaped to fit into the grooves 35, 36 on the lower piece 23. The wedges and the grooves provide an interlocking mechanism between the upper piece 24 and the lower piece 23 to restrain movement between them when positioned together in a closed relationship.

In terms of use of the appliance and a method of correcting an abnormal occlusion, the appliance can be made using known fabricating techniques for manufacture of prosthetic devices. The dental patient to be treated has a malocclusion like that shown in FIG. 1, which desirably should be corrected. The correction is effected by training the mandible to reside at a new at-rest location that is a distance horizontally and vertically removed from the current equilibrium position it occupied with respect to the maxilla. The desired distance of correction is referred to herein as the occlusal deviation.

Figure 2:
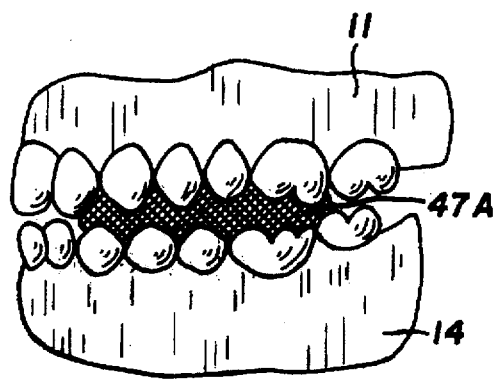
FIG. 2 is a side elevational view of the jaw and teeth of FIG. 1 being measured for a dental appliance using a wax bite impression technique.

The mouth of the patient is measured and fitted for the appliance. The initial fitting step is shown in FIG. 2. Wax impressions are taken of the upper and lower teeth. The mandible is moved forward in the direction of the desired correction. Depending upon the degree of correction, the mandible is moved forward the entire occlusal deviation or a portion thereof if the correction is to be effected in stages. A wax bite or registration material shown at 47A in FIG. 2 is taken of the new desired maxillary and mandibular relationship. The upper and lower appliance with the wedges and grooves are made to this new relationship of the maxillary and mandibular teeth. In FIG. 3, the mandible is moved forward a distance less than the total occlusal deviation, but one which will be comfortable to the patient for purposes of effecting an intermediate correction. The dental appliance 23 is in use at the position of intermediate correction. The upper piece 24 of appliance 22 is fitted to the posteriors of the maxilla or upper jaw 11. The lower piece 23 is fitted to both anterior and posterior teeth of the lower jaw 14. The groove 36 is positioned to accept the wedge 47 to hold the lower jaw 14 in an intermediately corrected position with respect to the upper jaw 11. An elastic binder assembly 49 of the type know in the art can be used to bias the upper and lower pieces 23, 24 together.

The lower and upper pieces 23, 24 of appliance 22 fit over the teeth in order that they may be held in place to maintain proper relationship between the wedge and groove mechanism. As shown, the lower piece 23 covers both the anterior and posterior teeth. A suitable anchor for the lower piece 23 could be devised using fewer than the entire set of lower teeth, for example, just the posteriors.

The flat occlusal surfaces on the upper and lower pieces in the region of the posterior teeth, are functional in the mechanics of chewing food, such that the dental appliance 22 can be worn continuously. The narrowed width of the anterior portion of the lower piece 23 is used in conjunction with the uncovered anterior upper teeth to bite in a manner that closely approximates an unencumbered bite.

The appliance 22 can provide the intermediate occlusal correction to the dental patient 10 is worn by the dental patient for a suitable period of time, for example, three months. At such time, the dental appliance 22 is adjusted to provide for additional correction of the occlusal deviation.

The wedges and grooves of the appliance can be located to hold the jaws in an over-corrected position. This is shown in FIG. 4 at 50. The overcompensation allows for a certain measure of settling once the appliance is discontinued.

Figure 9:
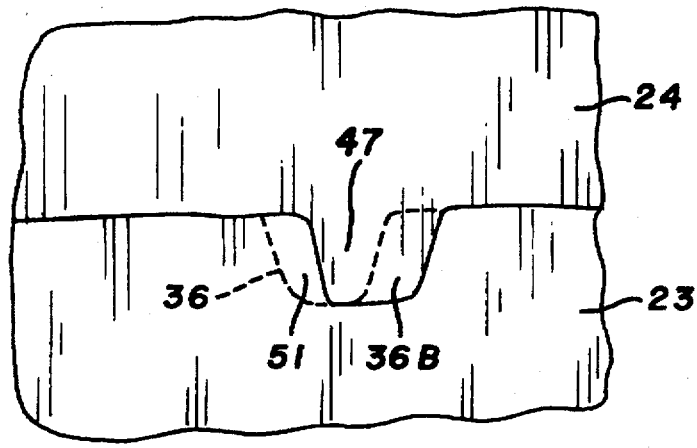
FIG. 9 is an enlarged schematic view of portions of the upper and lower pieces of the dental appliance of the invention is mating relationship and showing how the interlock position between the upper piece of the dental appliance and the lower piece, can be moved.

As shown in FIG. 9, the old groove is filled and a new groove is formed. The new groove, indicated at 36B, may simply be a continuation from the old groove. A filler material 51 is placed in the anterior portion of the old groove. Material is removed from the posterior edge of the old groove to form the new location. The lower piece 23 of the dental appliance, or at least that portion containing the groove, can be formed of an easily workable acrylic-type material that is subject to hardening by a suitable curing process. This makes adjustment of the positional relationship between the upper and lower pieces an easy procedure.

Upon fabrication of the second groove, the upper and lower pieces 23, 24 are installed in the mouth as previously indicated with the wedge 47 now registering in the relocated groove 36B. The dental appliance is worn in such a fashion until there are dental and skeletal changes to assume the new relative position with respect to the maxilla of its own volition. The elastic assembly 49, FIG. 3, assists in this effort. As before, the occlusal surfaces of the appliance permit eating, thus enabling the continuous wearing of the device.

Through the use of the appliance according to the present invention, there is a very definite positioning of the mandible during the correction of the malocclusion. The upper and lower occlusal surfaces are in total occlusion during the mechanics of eating, thus making it easier to chew food and enabling the appliance to be left in during meals. The treatment time is accordingly reduced because the appliance is left continually in the mouth of the patient (being removed only for purposes of brushing the teeth). Adjustment of the device is easily made by forming a new relationship of the wedge and groove mechanism. The device is easily installed and removed from the mouth. It can be formed of a partially elastic material for purposes of comfort. The appliance can be constructed to cover a minimum number of teeth, for example, just the posterior teeth, whereby the presence of the appliance being worn by the patient is less noticeable.

Figure 10:
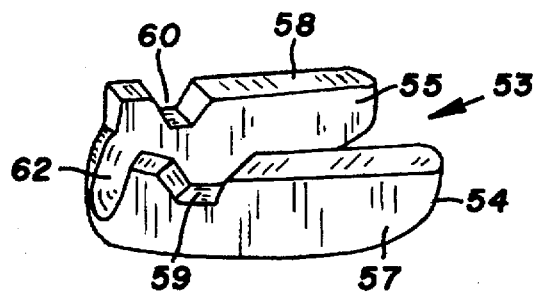
FIG. 10 is an upper perspective view of a lower dental piece like that of FIG. 6 showing an alternative embodiment.
Figure 11:
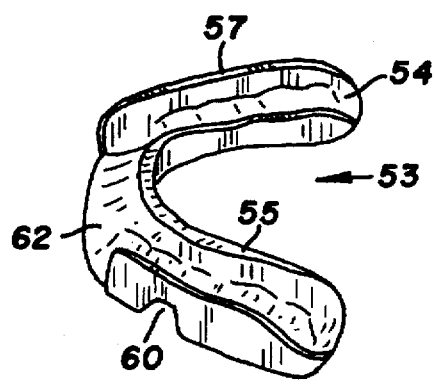
FIG. 11 is a perspective view showing the under portion of the lower dental piece of FIG. 11.

An alternative embodiment of a dental appliance lower piece is shown in FIG. 10 and 11, and indicated generally at 53. An arch-shaped body portion 54 is constructed to closely conform to the lower dental arch of the patient. The body portion 54 has an interior side wall 55 and an exterior side wall 57 forming a channel that accommodates the posterior mandibular teeth. A top wall 58 forms occlusal surfaces for chewing. Grooves 59, 60 are positioned for receipt of wedges from a corresponding top piece in order to retain the jaw in adjusted position.

The upper anterior section of the body portion 54 is cut away as at 62, thereby allowing eruption of mandibular teeth if an anterior open bite is present. The section of the body portion 54 covering the posterior mandibular teeth is sufficient to anchor the lower dental piece in place in order to secure it to the lower jaw.

Figure 12:
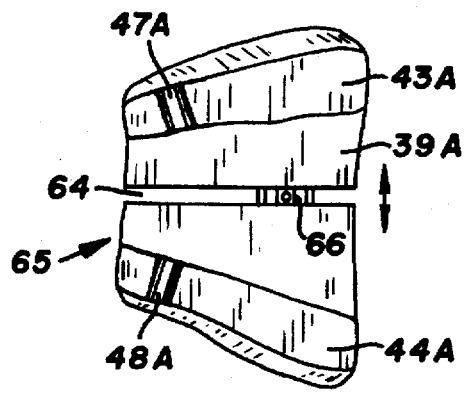
FIG. 12 is a bottom plan view of an upper dental piece showing a modification thereof, with a screw adjustment mechanism.

FIG. 12 illustrates an alternative embodiment of an upper piece according to the invention. This corresponds to the embodiment shown in FIGS. 6 and 8 with the addition of a screw adjustment to adjust the width of the upper piece. The upper piece 65 has a curved plate 39A to substantially conform to the roof of a mouth. The plate 39A terminates in side walls defining occlusal surfaces 43A, 44A which carry wedges 47A, 48A. A split 64 separates the upper piece 65 into equal and symmetric halves. A screw adjustment mechanism connects the two halves of the upper piece 64. The screw adjustment mechanism 66 can be like that shown in U.S. Pat. No. 5,242,304, issued to Lloyd H. Truax et al, on Sep. 7, 1993. This presents an expansion joint that allows the adjustment of the relative position between the left and right halves of the upper piece 65.

Figure 13:
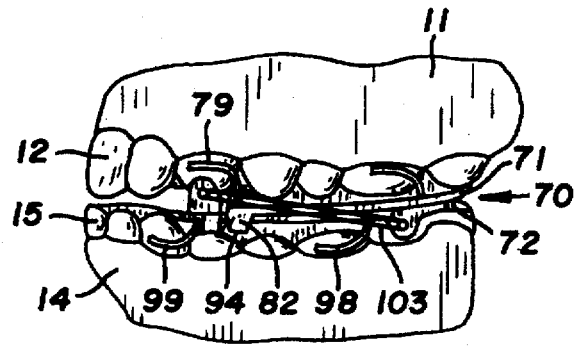
FIG. 13 is a side plan view of a human dental set having a dental appliance installed thereon according to a further modification of the invention.
Figure 14:
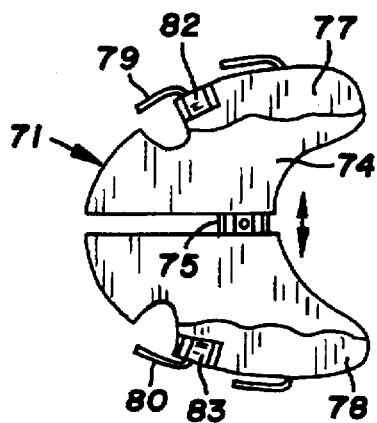
FIG. 14 is a bottom plan view of the upper piece of the dental appliance.
Figure 15:
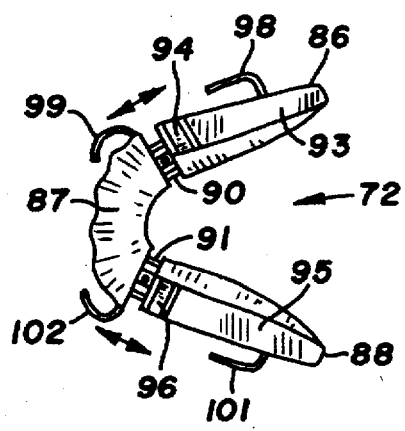
FIG. 15 is a top plan view of the lower piece of the dental appliance.

A yet further embodiment of a dental appliance according to the invention. is shown in FIGS. 13–15. In FIG. 13, the appliance is shown installed with respect to a patient with the upper jaw 11 and lower jaw 14, mandibular teeth 15 and maxillary teeth 12. The dental appliance 70 includes an upper piece 71 and a lower piece 72. The upper and lower pieces 71, 72 have a wedge/groove interlock. The respective pieces are held in place with respect to the jaws by clasps that engage the teeth of the individual.

The bottom plan view of the upper piece 71 is shown in FIG. 14. It includes a curved plate 74 shaped to conform to the roof of the mouth. The plate 74 is divided into two halves by a screw adjustment mechanism 75 of the type previously described. The plate 74 terminates in occlusal surfaces 77, 78. The clasps 79, 80 extend outwardly from the sides of the occlusal surfaces 77, 78 and are shaped to engage selected teeth of the dental patient. The occlusal surfaces carry interlocking wedges 82, 83.

The lower piece 72 is shown in plan view in FIG. 15. In composite, it is generally arch-shaped to conform to the lower arch of the patient. A lower piece includes an arch-shaped body portion having a right segment 86, a central segment 87 and a left segment 88. The segments are connected by screw adjustment mechanisms 90, 91 to permit other orthodontic correction of the patient during the procedure for adjustment for malocclusion.

The right segment 86 carries an occlusal surface 93 and an interlocking groove 94. The left segment 88 carries an occlusal surface 95 and a second interlocking groove 96.

A plurality of clasps are provided in order to secure the lower piece 72 with respect to the jaw. This includes right hand clamps 98, 99 located on the right side of the lower piece, and left hand clasps 101, 102 located on the left side. The right and left clasps 98–101 are rearwardly located extending from the right and left segments 86, 88. The right and left clasp 99, 102 are forwardly located, and are each located on the edges of the central segment 87. Each clasp is curved and is configured to fit around a selected tooth of the mandibular set of teeth of the patient. FIG. 13 shows the relationship of the various clasps and the teeth on the left side of the patient. A binder 103 is provided in order to bias the jaws in the closed position of correction with the interlocking wedges and grooves engaged.

While there has been shown and described a particular embodiment of a malocclusion correcting device according to the invention, it will be apparent that certain deviations can be had without departing from the scope of the invention.

The embodiments of the invention in which an exclusive property or privilege is claimed are defined as follows:

1. A method of making a dental appliance consisting of upper and lower dental pieces, to correct a malocclusion of a dental patient by moving the lower jaw of the patient with respect to the upper jaw, from a position of malocclusion toward a position of correction, by distance of an occlusal deviation, comprising the steps of:

making a lower dental form to fit the lower dental arch of the patient and having upwardly-facing posterior occlusal surfaces;

making an upward dental form to fit the upper dental arch of the patient and posterior teeth, with a downwardly-facing occlusal surfaces;

with the upper and lower dental forms fabricated to fit the dental patient by moving the mandible of the patient a distance of occlusal correction, closing the mandible upon a wax bite;

forming the dental appliance with an upper piece and a lower piece according to the wax bite with one of said pieces having a wedge and the other of said pieces having a groove fabricated at the positions formed on the wax bite.

2. A dental appliance produced according to the method of claim 1.

3. A method of correcting a malocclusion of a dental patient, by an amount of an occlusal deviation, comprising the steps of:

providing an upper dental piece constructed to orthodontically fit within the mouth of the patient, and releasably secured to selected upper teeth of the patient;

providing a lower dental piece constructed to orthodontically fit in the mouth of the patient, and releasably secured to selected lower teeth of the patient;

providing an interlock means between the dental pieces, including a wedge on a first of said dental pieces and;

providing a groove to the interlock means on the second of the dental pieces, the location of the wedge being offset from the groove by a distance of occlusal correction so that upon formation of the groove on the second piece, the first and second pieces will interlock with the jaws secured in a position of occlusal correction.

4. The method of claim 3 including:

the steps of first positioning the groove for a partial occlusal correction, then repositioning the groove for a more complete occlusal correction.

5. The method of claim 4 including:

providing bias means to influence the dental pieces in a closed position.

6. The method of claim 4 including the steps of:

providing binder assemblies to influence the dental pieces in a closed position.

7. A dental appliance for correction of a class II malocclusion, comprising:

an upper piece formed to fit into the upper portion of the mouth having (a) means to fit selected upper teeth to secure the upper piece to the upper jaw, (b) flat occlusal surfaces, and (c) a plurality of interlocking wedges, said wedges located on the occlusal surfaces;

a lower piece formed to fit into the lower portion of the mouth having (a) means to fit selected lower teeth to secure the lower piece to the lower jaw, (b) flat occlusal surfaces aligned with the occlusal surfaces of the upper piece, and (c) a plurality of grooves for interlocking with corresponding wedges on the upper piece, said grooves located on the occlusal surfaces;

said wedges and grooves adapted to releasably interlock in an anterior-posterior direction when the upper and the lower jaw are in a substantially closed position to hold the upper piece relative to the lower piece in an anterior-posterior position; and the wedges positioned on the upper piece relative to the position of the corresponding grooves on the lower piece a predetermined distance substantially equal to a class II malocclusion deviation.

8. A dental appliance for correction of a Class II Malocclusion, comprising:

an upper piece formed to fit into the upper portion of the mouth having means to fit selected upper teeth to secure the upper piece to the upper jaw;

said upper piece having a plurality of a first part of an interlocking means;

a lower piece formed to fit into the lower portion of the mouth having means to fit selected lower teeth to secure the lower piece to the lower jaw;

said lower piece having a plurality of a second part of an interlocking means;

said first and second parts of the interlocking means adapted to releasably interlock in an anterior-posterior direction when the upper jaw and the lower jaw are in a substantially closed position to hold the upper piece relative to the lower piece in an anterior-posterior position; and said first part of the interlocking means positioned on the upper piece relative to the position of the second part of the interlocking means on the lower piece a predetermined distance substantially equal to a Class II Malocclusion deviation.

9. The dental appliance of claim 8 wherein:

said first part of the interlocking means is a wedge and the second part is a groove.

10. The dental appliance of claim 8 wherein:

said upper piece has occlusal surfaces, said lower piece having occlusal surfaces aligned with the occlusal surfaces of the upper piece, said interlocking means located on the occlusal surfaces.

11. The dental appliance of claim 10 wherein:

one part of the interlocking means is a wedge and the other part of the interlocking means is a groove.

12. The dental appliance of claim 10, wherein the occlusal surfaces of the upper and lower pieces are flat.

13. The dental appliance of claim 8 wherein:

said upper piece includes a plate to be installed in the roof of the mouth or upper teeth, and channel portions having lateral edges to fit posterior upper teeth, and occlusal surfaces downwardly facing on the channel portions;

said lower piece being an arch-shaped member with a channel-shaped cross section formed to fit over the lower dental arch of the patient, and occlusal surfaces on the upper surfaces of the member in the vicinity of the posterior teeth; and said first and second parts of the interlocking means being located on the occlusal surfaces of the upper and lower pieces.

14. The dental appliance of claim 13 wherein:

one part of the interlocking means is a wedge and the other part is a groove.

15. The dental appliance of claim 14 including:

a binder means to bias the first and second pieces of the dental appliance in a closed position.

16. The dental appliance of claim 8 wherein:

the parts of the interlock means are relatively positioned to hold the lower jaw with respect to the upper jaw in a position of overcorrection of the malocclusion.

* * * * *